United States Patent
Zaret et al.

(10) Patent No.: US 8,802,432 B2
(45) Date of Patent: Aug. 12, 2014

(54) METHODS AND CELL CULTURES FOR PROMOTING ORGANOGENESIS AND TISSUE DEVELOPMENT

(75) Inventors: Kenneth S. Zaret, Elkins Park, PA (US); Kunio Matsumoto, Ibaraka (JP); Hideyuki Yoshitomi, Philadelphia, PA (US)

(73) Assignee: Fox Chase Cancer Center, Philadelphia, PA (US)

( * ) Notice: Subject to any disclaimer, the term of this patent is extended or adjusted under 35 U.S.C. 154(b) by 695 days.

(21) Appl. No.: 10/487,878

(22) PCT Filed: Sep. 6, 2002

(86) PCT No.: PCT/US02/28607
§ 371 (c)(1), (2), (4) Date: Sep. 20, 2004

(87) PCT Pub. No.: WO03/023019
PCT Pub. Date: Mar. 20, 2003

(65) Prior Publication Data
US 2005/0042750 A1 Feb. 24, 2005

Related U.S. Application Data

(60) Provisional application No. 60/318,144, filed on Sep. 7, 2001.

(51) Int. Cl.
*C12N 5/071* (2010.01)
*C12N 5/00* (2006.01)
*C12N 5/074* (2010.01)

(52) U.S. Cl.
CPC ............ *C12N 5/0671* (2013.01); *C12N 5/0672* (2013.01); *C12N 5/069* (2013.01); *C12N 2502/28* (2013.01)
USPC ............ 435/373; 435/370; 435/347; 435/377

(58) Field of Classification Search
CPC .... C12N 5/0671; C12N 5/0672; C12N 5/069; C12N 2502/28
USPC .................................. 435/347, 370, 373, 377
See application file for complete search history.

(56) References Cited

U.S. PATENT DOCUMENTS

| 5,364,785 A | 11/1994 | Mather et al. ............. 435/240.2 |
| 6,146,889 A | 11/2000 | Reid et al. ..................... 435/325 |
| 6,197,575 B1 * | 3/2001 | Griffith et al. ............. 435/288.4 |

OTHER PUBLICATIONS

Powers et al. 1998. Adhesion-Guided in Vitro Morphogenesis in Pure and Mixed Cell Cultures. Microsc. Res. Tech. 43:379-384.*
Hamazaki et al. 2001. Hepatic maturation in differentiating embryonic stem cells in vitro. FEBS Letters 497:15-19.*
Nessi et al. 1981. Foetal Haemopoiesis During the Hepatic Period. I. Relation Between In Vitro Liver Organogenesis and Erythropoietic Function. The Anatomical Record 200:221-230.*
Duncan. 2003. Mechanisms controlling early development of the liver. Mechanisms of Development. 120:19-33.*
Dasdia et al. 1998. Organ Culture in 3-Dimensional Matrix: In Vitro Model for Evaluating Biological Compliance of Synthetic Meshes for Abdominal Wall Repair. J Biomed Mater Res (Appl Biomater) 43: 204-209.*
Matsumoto et al. 2001. Liver Organogenesis Promoted by Endothelial Cells Prior to Vascular Function. Science vol. 294. p. 559-563.*
The Edinburgh Mouse Atlas:Staging Criteria. 2010. downloaded from http://genex.hgu.mrc.ac.uk/Databases/Anatomy/MAstaging.shtml. p. 1-4.*
Altmann et al. Behavior of fetal intestinal organ culture explanted onto a collagen substratum. Development 110, 353-370 (1990).*
Griffith et al. In Vitro Organogenesis of Liver Tissue. Annals of the New York Academy of Sciences vol. 831, pp. 382-397,Dec. 1997.*
HUVEC. 2009. Cascade Biologics, GIBCO. p. 1-3.*
HepG2 product sheet. ATCC p. 1-3, 2013.*
DMEM. Product Information from Sigma-Aldrich. 1998, p. 1-2.*

* cited by examiner

*Primary Examiner* — Taeyoon Kim
(74) *Attorney, Agent, or Firm* — Licata & Tyrrell P.C.

(57) ABSTRACT

Methods of promoting liver morphogenesis prior to the functioning of blood vessels by culturing liver cells with endothelial cells is provided. Also provided are cell cultures and method of promoting vasculogenesis of liver tissue by contacting liver cells with endothelial cells.

3 Claims, No Drawings

METHODS AND CELL CULTURES FOR PROMOTING ORGANOGENESIS AND TISSUE DEVELOPMENT

INTRODUCTION

This invention was funded in part by the National Institutes of Health, grant number GM36477 and a cancer core center grant to Fox Chase Cancer Center (FCCC). The United States Government may have certain rights in this invention.

FIELD OF THE INVENTION

This invention relates to method and cell cultures for promoting cell differentiation, organogenesis, and tissue development by endothelial and blood vessel cells, independent of the blood supply.

BACKGROUND OF THE INVENTION

The mechanisms by which tissue morphogenesis initiates from the gut endoderm are not well defined. Although genetic methods have yet to provide much insight into hepatic specification and subsequent cell interactions, experiments with transplanted tissues have revealed more information. Hepatocytes develop from the endoderm lining the presumptive ventral foregut, near the developing heart. At about 9 days gestation in the mouse, foregut endoderm in contact with cardiac mesoderm proliferates more rapidly, and first α-fetoprotein (AFP) and then serum albumin mRNAs become detectable by in situ hybridization (Shiojiri et al. 1991. *Cancer Res.* 51:2611-2620) By 9.5 days gestation, hepatic endodermal cells migrate into the more posterior mesenchyme of the septum transversum, where they begin to form the liver. Each tissue has its own architectural constraints on how the vascular system must integrate with functional aspects of an organ. To construct a vascular system that is specific for the needs of a particular organ, the development of the vascular system must be carefully coordinated with the development of the parenchymal cells. Assembly into a nascent organ may be regulated through interactions between parenchymal cells and vascular endothelial cells during organ morphogenesis. Understanding vascular development coordination with organogenesis will provide insights into future efforts to reconstitute organ systems for medical purposes and to generate tissue types in vitro for research, toxicological, and pharmaceutical applications.

Despite the clear importance of understanding these principles, very little is known about the earliest steps of vasculogenesis during organ development. Vasculogenesis refers to the earliest stages of vascular development, during which vascular endothelial cell precursors undergo differentiation and coalesce to form a network of primitive tubules (Risau, W. 1997. *Nature* 386: 671-674). This initial lattice, consisting purely of endothelial cells, is then remodeled by a process referred to as angiogenesis (Risau, W. 1997. *Nature* 386: 671-674), which involves the sprouting, branching, and differential growth of blood vessels to form the more mature vasculatures seen in the adult organs. Angiogenic vascular development also involves the sprouting and penetration of vessels into previously avascular regions of the embryo (Folkman, J. and D'Amore, P. A. 1996. *Cell* 87:1153-1155; Lindahl, et al. 1997. *Science* 277: 242-245). Mechanisms of vascular development during organogenesis, particularly of the liver, are unknown and vasculogenesis, angiogenesis, or both may possibly be involved.

It is known that close proximity to the cardiac mesoderm with the foregut endoderm causes the foregut endoderm to develop into the liver (LeDouarin, N. M. 1975, *Med. Biol.* 53, 427-455). This initial induction is accompanied by the activation of liver genes and enhanced proliferation of the newly specified hepatic cells (Gualdi et al. 1996; Jung et al. 1999). In a second step, these hepatic cells migrate and/or proliferate into the adjacent septum transversum, generating the liver bud. This morphogenetic transition, from hepatic endoderm to liver bud, represents the major defining moment in converting a simple epithelium to a complex structure that establishes the foundation for organogenesis. Although it is known that mesenchyme cells in the septum transversum promote this transition (LeDouarin, N. M. 1975. Med. Biol. 53, 427-455; Rossi, J. M., Dunn, N. R., Hogan, B. L. M., and Zaret, K. S. 2001, Genes Dev. 15:1998-2009) the potential role of other cell types is unknown.

SUMMARY OF THE INVENTION

The present invention provides a method of promoting vasculogenesis of liver tissue by maintaining contact of liver cells with endothelial cells and early vascular structures to promote morphogenetic development of liver cells and liver tissue.

The present invention further provides a method of promoting liver organogenesis prior to the functioning of blood vessels comprising culturing liver cells with endothelial cells.

The present invention further provides cell cultures and methods for promoting vessel formation among liver cells using cell cultures comprising hepatic cells and human endothelial cells in a mixture of hepatic cell media and endothelial cell media.

DETAILED DESCRIPTION OF THE INVENTION

The well ordered stages of early visceral organ development serve as a model for changes in cells and tissues that occur in various biological contexts. During tissue specification, epithelial cells receive stimuli that cause changes in gene expression and cell division. The cells then begin to differentiate and proliferate within the epithelium and gain the capacity to move into surrounding connective tissue. The cells then form a new domain of condensed tissue mass which becomes vascularized. These transitions require the careful orchestration of signals between epithelial cells, mesenchymal cells and endothelial cells. The hypothesis addressed by the work leading to this application is that during organ development, endothelial cells promote epithelial morphogenesis and outgrowth prior to the functioning of the vasculature.

The term vasculogenesis refers to the earliest stages of vascular development during which angioblasts differentiate and coalesce to form a network of primitive endothelial tubules. This initial lattice made up solely of endothelial cells, is subsequently remodeled by angiogenesis. Angiogenesis involves the sprouting, branching, and differential growth of blood vessels into avascular regions to form more mature vasculatures as seen in the adult tissues.

Each tissue has its own functional constraints on the architecture of its vascular system. The liver is highly vascularized by distinct capillary structures known as sinusoids. The sinusoids are radially distributed and line hepatocyte plates from the portal tracts, which contain branches of the portal vein and hepatic artery, to the central veins. Postnatally, the hepatic vasculature is critical for liver functions, including the acquisition and metabolism of nutrients, protection of the liver from inflammatory responses and harboring of resident macrophages. Before birth, a hepatic vasculature is necessary for the liver to function as a hematopoietic organ. Hepatic induction of the endoderm occurs by embryonic day 8.5 of gestation of the mouse (and about 2-3 weeks in the human), and hematopoetic cell invasion of the liver occurs by E10 in the mouse so that rapid vascular development is essential.

While the liver vasculature was initially thought to originate by hepatic cell migration into a segment of the nearby vitelline veins, more detailed studies have revealed vasculogenesis within the adjacent septum transversum mesenchyme. Specifically, chick-quail chimera studies and other approaches revealed that splanchnopleural angioblasts contribute to vasculogenesis throughout the endoderm derived organs; the angioblasts apparently being induced by the endoderm itself.

Cells in the embryonic septum transversum surround the midgut endoderm after hepatic induction by the cardiac mesoderm, and have been shown to elicit a secondary morphogenetic induction upon the nascent liver bud. Transcription factor expression in the septum transversum mesenchymal cells is critical for morphogenetic outgrowth of the liver. Also, the septum transversum is believed to contain vasculogenic endothelial cells, prior to the invasion of the hepatic endoderm, and the presence of such cells correlates with hepatic endoderm and hepatic morphogenesis. Due to a lack of early endothelial cell markers or genetic mutations that cleanly eliminate endothelial cell lineages, prior studies did not definitively assess the potential contribution of angioblasts or early endothelial cells to the secondary morphogenetic induction of the liver or other endoderm-derived organs.

The present invention employs specific endothelial cell markers, a mouse line in which endothelial cell development is blocked, and a novel liver bud culture system to assess the role of vasculogenic endothelial cells in the earliest phases of organ morphogenesis.

One aspect of the present invention relates to methods of promoting morphogenesis of liver tissue by maintaining cell to cell interactions between liver hepatocytes and endothelial cells. For example, in one embodiment, E8.5-E9.5 liver bud tissue is cultured, at the air-gas interface on a Transwell membrane, with 0.2% or 5% MATRIGEL in the culture medium. This culturing permits extensive growth and morphogenesis. Maintenance of contact between the liver cells and the endothelial cells or transient contact between these cells is considered physical interaction. Interaction does not necessarily need to be direct physical contact; interaction may also be mediated by secreted molecules such as growth factors, peptides, or extracellular matrix molecules. The liver cells are preferably nascent hepatic cells, however, they may also be derived from any other hepatic cell precursor, for example, non-liver lineages, such as stem cells.

Another aspect of the present invention relates to methods of promoting liver morphogenesis prior to the functioning of blood vessels comprising culturing liver cells with endothelial cells to produce interactions sufficient to permit liver tissue morphogenesis. Interactions include maintenance of contact between the liver cells and the endothelial cells or transient contact. Interaction does not necessarily need to be direct physical contact. Interaction may also be mediated by secreted molecules such as growth factors, peptides, or extracellular matrix molecules. The liver cells are preferably nascent hepatic cells, however, they may also be derived from any other hepatic cell precursor, for example, stem cells.

It was found that endothelial cells interacting with newly specified hepatic cells can be detected prior to blood vessel formation, which is earlier than anticipated. It is therefore believed that such endodermal cells are critical for the outgrowth of the hepatic endoderm. Given the results, and similarities between organogenesis, liver regeneration and tumorigenesis, it is believed that endothelial cells play roles, earlier than previously believed, in each of these critical biological processes.

At 8.5-9.0 days, newly specified hepatic cells begin to multiply within the endodermal epithelium. At E9.5 the hepatic cells migrate into the surrounding septum transversum mesenchyme. Occasionally at E9.5 and clearly at E10.5, darkly stained hematopoetic cells within developing sinusoids can be seen in the liver region. To determine when angioblasts or endothelial cells begin to be associated with the liver bud, the sections were stained with an antibody against platelet endothelial-cell adhesion molecule PE-CAM, CD31. PE-CAM is a definitive marker for embryonic endothelial cells. As a second marker, β-galactosidase staining of heterozygous mice, in which the LacZ gene had been recombined into the flk-1 locus resulting in Lac-Z expression reflecting that of the native flk-1 gene, was performed. Flk-1 (VEGFR-2) is a cell surface receptor or vascular endothelial growth factor (VEGF) and is highly expressed in embryonic angioblasts and endothelial cells. Although flk-1 homozygotes are embryonic lethal, heterozygous embryos are normal. PE-CAM and flk-1 lacZ positive cells lined the nascent sinusoids that contained the hematopoetic cells at E9.5-E10.5. Notably, the nascent sinusoids at E9.5 were irregular and consisted mostly of small vascular structures lined by endothelial cells which only occasionally had been invaded by hematopoietic cells.

Unexpectedly, angioblasts or endothelial cells were detected as early as E8.5-9.0 as a loose necklace of cells interceding between the thickening hepatic epithelium and the septum transversum mesenchyme. At E9.0, where occasional segments of the hepatic endoderm begin to break into the mesenchyme, the angioblasts or endothelial cells interceded between the tissue types. During these E8.5-9.0 stages, the endothelial cells were separated from one another, and closed vascular structures or local hematopoetic cells were not detected. Strikingly, even at E9.5, when the endothelial cells were separated from one another, closed vascular structures or local hematopoetic cells were not detected. At E9.5, when the endothelial cells first began to be organized into vascular structures within the liver bud, they delimited the domain of septum transversum mesenchyme into which the hepatic cells migrated. No hepatic cells were detected beyond the endothelial cell domain, although endothelial structures were seen beyond the hepatic domain. These findings demonstrate that prior to blood vessel formation and function, angioblasts or endothelial cells physically interact with nascent hepatic cells. This interaction precedes liver bud emergence and persists from the hepatic endoderm stage through the formation of the liver proper.

To determine whether endothelial cells promote hepatic morphogenesis, flk-1 heterozygous mice were crossed to generate homozygous embryos. Such embryos are from early angioblasts but not mature endothelial cells or blood vessels, and the mutant angioblasts are defective in migrating to their normal sites of vasculogenesis. When flk-1−/− embryos at E9.0 were stained for β-galactosidase and sectioned, no angioblasts or endothelial cells were evident, by morphology or staining, around the hepatic endoderm or in the septum transversum mesenchyme. In such embryos, the hepatic endoderm began to thicken normally, reflecting that hepatic induction had taken place and liver genes are activated.

It has been previously observed that the homozygous flk-1 allele caused embryonic lethality by E10.5, and that embryos at E9.5 were smaller than their heterozygous littermates but had similar numbers of somites. The retarded growth of the homozygous flk-1 embryos, compared to heterozygotes, is evident by comparing embryo sizes in the transverse sections. The flk-1-/- embryos exhibited growth between the E9.0 and the E9.5 stages including enhanced closure of the neural tube, narrowing of the gut, and increased area of the septum transversum mesenchyme cells, in addition to an increase in somite number. Most importantly, despite these changes in embryonic growth over the E9.0 to E9.5 period, the size of the hepatic endoderm remained constant. In the E9.5 embryos there was no evidence of the hepatic cells migrating into the surrounding septum transversum mesenchyme. In contrast, in flk-1 heterozygous and wild type embryos at E9.5, extensive hepatic cell migration had occurred. It is believed that the presence of angioblasts and/or early endothelial cells is critical for hepatic morphogenesis prior to hematopoetic cell invasion.

Another aspect of the present invention relates to methods of promoting liver morphogenesis prior to the formation of blood vessels comprising culturing liver cells with endothelial cells. Preferably the liver cells are liver bud tissue, though they may be hepatic cells derived from adult liver, liver tumors, or other cell types such as stem cells. An embryo tissue explant system was used to determine whether endothelial cells within and around the liver bud are critical to promote hepatic growth in isolation of the rest of the embryo. It was found that culturing E8.5-E9.5 liver bud tissue at the air-gas interface on a Transwell membrane, with 0.2% or 5% MATRIGEL in the culture medium, permitted extensive growth and morphogenesis.

Explants from E9.5 embryos that were fixed two hours after starting the culture were stained for PECAM (Platelet-Endothelial Cell Adhesion Molecule). Isolated PECAM positive cells and cell clusters were evident but no vasculature was detected. After 9 hours in culture, the explants flattened out into the membrane, becoming difficult to see, yet PECAM staining revealed the beginning of vascular development. By 24 hours, a web of vessel like structures was prominent throughout the explants. By 72 hours, a remarkable extent of vascular development and overall growth had occurred. Transverse section of the 72 hours explants revealed the thickness of the tissue and the presence of vascular structures throughout. Higher magnification showed that the explants formed small, lumenized vessels, and larger vascular structures which were lined by PECAM positive cells analogous to that seen in liver buds in embryos. Explants from flk-1 lacZ heterozygous embryos also exhibited a web of vascular structures upon staining for β-galactosidase, reflecting flk-1 gene activity. In situ hybridization on the same explant showed that most of the flk-1 lacZ positive tissue, i.e. the vascularized region, expressed serum albumin mRNA. It is believed that the new culture conditions were permissive for de novo vascular development of the liver, in the absence of other potential influences outside of the liver bud domain. The culture method also revealed that the vascularized region in vitro almost completely co-localizes with the hepatic cell region, analogous to what is observed in the emerging liver bud.

Several approaches were employed to investigate the necessity of endothelial cells to promote hepatic morphogenesis. First, the growth of wild type flk-1 heterozygous and flk-1 homozygous mutant liver bud tissue cultivated in vitro was examined. To monitor the growth of the hepatic domain, explant cultures were established and allowed to grow for 72 hours, during which time they were photographed and ultimately subjected to in situ hybridization for serum albumin mRNA. Explants cultured for one hour remained on top of the membrane and resulted in refraction of the light in the surrounding medium. By 72 hours, the primary thick masses of tissue became surrounded by a thin layer of spindally fibroblastic cells that grew out of the original explant. The fibroblasts are believed to be derived from septum transversum mesenchyme cells. After 72 hours, the primary thick mass of cells in the center of the wild type and heterozygous explants expressed albumin mRNA. The cellular area of the explants was quantitated and it was found that for wild type and heterozygous flk-1 the total area spanned by the tissue explants, including the fibroblastic cells, increased about fifteen-fold over the 72 hour period.

The flk-1 homozygous mutant explants were usually smaller at the outset, but they too exhibited about a fifteen-fold increase in overall cellular area during the 72 hour growth period. The primary thick tissue mass portion of the flk-1 homozygous explants usually remained small, and most of the growth was exhibited by the fibroblastic cells. To quantitate the growth of the hepatic cells, the area of albumin mRNA-positive cells, i.e. the hepatic domain, was compared to the total cell area for wild type, heterozygous and homozygous flk-1 explants. The hepatic domain of wild type and heterozygous explants grew comparably to about twenty percent of the total cell area, while the hepatic domain of the homozygous flk-1 explants grew to only about five percent of the total cell area. The difference in growth was statistically significant, even though the hepatic endoderm incorporated bromodeoxyuridine in both the normal and the homozygous mutant explants. The lack of endothelial cells in the flk-1 explants specifically affects the outgrowth of the hepatic endoderm, while not affecting the growth of surrounding mesenchymal fibroblasts nor the initial expression of early liver genes in the endoderm. Further, the hepatic outgrowth induced by endothelial cells in the wild type and heterozygous explants occurs in isolation from the rest of the embryo.

As a second approach to investigate the necessity of endothelial cells for early hepatic morphogenesis, the growth and development of endothelial cells in liver bud explants from wild type embryos was inhibited. This approach determined whether the endothelial cells are needed continuously or whether they solely provide an initial stimulatory signal that, for example, is perpetuated by the hepatic or the septum transversum mesenchyme cells. A newly identified angiogenesis inhibitor, NK4, which suppresses tumor growth and metastasis was utilized. NK4 contains four kringle domains of hepatocyte growth factor (HGF) and was initially identified as an HGP-antagonist. NK4 has structural similarity to angiostatin, a kringle domain containing an internal fragment of plasminogen.

Liver buds isolated from E9.5 embryos were cultured as above in the presence or absence of NK4 and then subjected to PECAM staining to detect endothelial networks, and then hematoxylin to visualize the primary cell mass after PECAM staining. In contrast to the extensive vascular networks seen in the control cultures, vascular network formation was strongly inhibited in 6 of 6 explants treated with 500 nM NK4. In all such cultures, growth of the primary tissue mass was greatly inhibited.

NK4 is an HGF-antagonist as well as an angiogenesis inhibitor and the expression of HGF in the septum transversum mesenchyme, as well as that of the HGF receptor, c-met, in hepatic cells is critical for liver development. It is believed that NK4 may affect hepatic growth independently of vascular network formation. It is noted that homozygous inactivation of either the HGF or c-met genes results in liver growth defects after the emergence of the liver bud. To address the possible role of HGF as a direct regulator of hepatic outgrowth in the explant system, liver buds were cultured with 500 nM NK4 and 25 nM recombinant HGF, the latter being a sufficient concentration to at least partially overcome the inhibitory effects of NK4 on HGF signaling. Both vascular development and primary tissue mass growth were inhibited. The addition of 0.3 nM HGF alone or 25 nM HGF did not induce a significant change in vascular network formation and outgrowth of the liver bud, nor did the presence of neutralizing antibody specific for HGF. The lack of effect of HGF or an HGF antagonist on the initial phase of hepatic endoderm outgrowth in vitro is consistent with the gene disruption studies showing that these factors are critical after liver bud emergence in embryos. In summary, these results indicate that NK4-inhibited vascular development causes a failure in liver bud growth. Based upon these findings it is believed that endothelial cells are needed continuously to promote early hepatic morphogenesis.

In another embodiment, hepatic cell lines co-cultured with normal human umbilical vein endothelial cells (HUVEC) resulted in vessel formation and enhanced cell function and differentiation. Surprisingly, it was found that when hepatic cells were co-cultured with HUVEC cells in hepatic media, the HUVEC cells die. When hepatic cells were co-cultured with HUVEC cells in HUVEC media, the hepatic cells died. It was only when hepatic cells were co-cultured with HUVEC cells in a mixture of HUVEC media and hepatic media the cell lines resulted in successful vessel formation with enhanced cell function. Accordingly, the present invention provides new cell cultures comprising hepatic cells and human endothelial cells in a mixture of hepatic cell media and endothelial cell media as well as methods for using these cell cultures in vessel formation and enhanced cell function.

It was also found that hepatic cell lines co-cultured with HUVEC successfully resulted in vessel formation and enhanced cell function in differing ratios of HUVEC media to hepatic media. In a preferred embodiment, the ratio of HUVEC media to hepatic cell media is 1:1; however other ratios such as 10:1 and 20:1 were also found to be successful in producing vessel formation and enhanced cell function. The hepatic cell line media was 45% DMEM, 45% Ham's F-12, 10% fetal calf serum, and 10 micrograms per ml. of insulin. Hepatic cell line HepG2 was co-cultured with HUVEC cells (BioWhittaker, Inc., East Rutherford, N.J.). The HUVEC media (Clonetics EGM BulletKit CC-3162; BioWhittaker, Inc., East Rutherford, N.J.) contained 500 ml of Endothelial Cell Basal Medium-2 and growth supplements Hydrocortisone, hFGF-B, VEGF, R3-IGF-1, Ascorbic Acid, Heparin, FBS, hEGF, and GA-1000. The hepatic and endothelial cells were able to be successfully grown on either a Transwell membrane or a plastic plating dish.

Despite the intense focus of many groups on the mechanisms of induction of endothelial cells and vascular structures in development, tissue regeneration, tissue repair and tumorigenesis, there has been little insight into the role of endothelial cells or vascular structures per se, in promoting organogenesis and other epithelial cell transitions. It has been discovered that angioblasts or early endothelial cells interact with newly specified hepatic endoderm, prior to liver bud emergence, and that the presence of endothelial cells intrinsically promote hepatic morphogenesis. The formation or structure of the blood vessels themselves is a necessary step, prior to the function of the vessels in providing oxygenation of blood cells to the liver region. It is well established that oxygenation is critical for tissue development and that oncostatin M signaling from hematopoetic cells specifically promotes liver development, confirming the necessity of blood vessel function in organogenesis. The earlier role of endothelial cell function that has been identified is presumed to be via a paracrine signaling mechanism that acts on neighboring epithelial cells. As the liver vasculature forms, the endothelial cells express new cell surface and extracellular matrix proteins some of which could be critical for promoting organ growth. The role of such proteins in promoting adult hepatocyte differentiation and morphogenesis is well known.

Experiments have also been conducted showing embryonic angioblasts or early endothelial cells to associate with newly specified cells of the lung, stomach, and pancreas were discovered, suggesting that despite the unique architectural features of the liver vasculature, endothelial cells may play early morphogenic roles in those tissues as well. Various aspects of organogenesis, such as epithelial cell proliferation and movement are also exhibited during tissue repair, liver regeneration in particular and tumorigenesis. Thus, the understanding of how endothelial cells promote early organogenesis will impact the understanding of these other processes as well as provide insights into future efforts to reconstitute organ systems for therapeutic purposes.

As will be understood by one skilled in the art upon reading of this disclosure, the methods of the present invention are particularly useful to create vascularized liver tissue; to development of replacement organs which would reconstitute mature organ function by a transplant patient; and to promote regeneration of lost or damaged hepatic tissue or organs in a patient as the cells of the present invention may be injected into humans to repair or replace damaged liver tissue. The cells of the present invention can also be used for in vitro studies of liver function; for example in drug screening assays where liver differentiation is critical.

The invention is further illustrated by the following non-limiting examples.

EXAMPLE 1

Embryo Preparation and Dissection

C3H mice were used for most of the wild-type studies and flk-1 LacZ mice were bred, genotyped and analyzed for β-galactosidase expression (Shalaby et al. 1995 Nature 376:62). Noon of the day of the vaginal plug discovery was taken to be 0.5 days gestation. For embryo dissections, the embryos were rinsed in phosphate-buffered saline (PBS), dissected free of decidual tissue, and transferred to black-wax dissecting dishes containing PBS. Under a stereomicroscope, E9.5 embryos were cut transversely caudal to the liver bud and the liver bud region was carefully dissected using electrolytically etched tungsten needles. Isolated liver buds were transferred onto Transwell polycarbonate filter membranes coated with type I collagen, in 12 or 24 separate wells of a culture plate containing 250 µl or 600 µl culture medium, respectfully, in the lower compartment. The tissue was cultured in Dulbecco's modified Eagle's medium (DMEM) containing 0.38% (w/v) $NaHCO_3$, 10% calf serum, 0.2% or 5% Matrigel (Becton Dickenson), 100 units/ml penicillin and 100 µg/ml streptomycin at 37° C. in humidified atmosphere of 5% carbon dioxide and 95% air. The phenotypic effects of the flk-1 homozygous mutant explants were clearer in 0.2% MATRIGEL.

EXAMPLE 2

Immunohistochemical Detection of Endothelial Cells

Rat anti-PECAM, CD31 monoclonal antibody was from PharMingen. Human NK4 or HGF/NK4, was purified from elastase-treated human hepatocyte growth factor, by methods known in the art. Anti-rat HGF antibody was raised in rabbits by immunizing with rat recombinant HGF and IgG was purified from the antisera using protein A-sepharose in accordance with known methods in the art. 1 µg/ml anti-rat HGF IgG almost completely neutralizes the biological activity of 1 ng/ml rat and mouse HGF.

For immunohistochemical detection of endothelial cells in mouse embryo, rat monoclonal antibody MEC13.3 (PharMingen, San Diego, Calif.) to mouse PECAM was used. Embryos were rinsed with PBS and fixed in PBS containing 4% paraformaldehyde at 4° C. overnight. The fixed embryos were rinsed in PBS, dehydrated in an ethanol series (70%, 80%, 90%, and 100% for a few hours each at 4° C.) and embedded in paraffin. Tissue sections were rehydrated and treated with 0.3% $H_2O_2$ in PBS for 15 minutes at room temperature. Sections were incubated with PBS containing 1.5% normal rabbit serum. Sections were then incubated with peroxidase-conjugated streptavidin-biotin complex for one hour. Sections were washed with PBS and the peroxidase staining was performed by incubating sections in 50 mM Tris-HCl buffer containing 0.05% $H_2O_2$ and 0.2% diaminobenzidine. The staining reaction was stopped by rinsing in $H_2O$ and sections were stained with hematoxylin.

For immunohistochemical detection of endothelial cells in cultures of liver bud explant, cells were fixed in PBS containing 4% paraformaldehyde at 4° C. overnight. Cells were rinsed with PBS and dehydrated in a series of methanol (25%, 50%, 75% and 100% at 4° C.). The dehydrated explants were bleached in methanol containing 5% $H_2O_2$ for 1 hour at room temperature. Cells were rehydrated, blocked in PBSMT (PBS containing 3% instant skim milk and 0.1% Triton X-100) for 30 minutes twice and incubated with anti-PECAM antibody (30 µg/ml IgG in PBSMT containing 1.5% normal rabbit serum) at 4° C. overnight. Cells were washed with PBSMT five times (twenty minutes each) and incubated with rabbit biotinylated anti-rat IgG at 4° C. for 6 to 8 hours. After washing with PBSMT 5 times, for 20 minutes each wash, cells were incubated with peroxidase-conjugated streptavidin-biotin complex in 0.2×PBSMT at 4° C. overnight. Cells were washed in PBSMT 5 times, for 20 minutes each, and finally in PBT (PBS containing 0.2% BSA and 0.1% Triton X-100) for 20 minutes. Cells were incubated in 0.3 mg/ml diaminobenzidine, 0.5% $NiCl_2$ in PBT followed by the addition of $H_2O_2$ to the final concentration of 0.02%. The staining reaction was stopped by rinsing in PBT and then PBS. The stained explants were postfixed in 2% paraformaldehyde, 0.1% glutaraldehyde in PBS at 4° C. overnight. In some experiments, the stained explants were dehydrated in the series of ethanol, treated with xylene and embedded in paraffin. The explants were sectioned 5 µm in thickness, deparaffinized and stained with hematoxylin.

EXAMPLE 3

In Situ Hybridization

Liver bud explants were subjected to double or single staining of β-galactosidase and in situ hybridization of albumin mRNA. After 72 hours in culture, cells were fixed in PBS containing 4% paraformaldehyde on ice for 1 hour. Following 2 washes with PBS for 5 minutes per wash, cells were incubated in PBS containing 5 mM potassium ferricyanide, 5 mM potassium ferrocyanide, 1 ng/ml x-gal, 2 mM $MgCl_2$, and 0.02% NP-40 at 37° C. overnight. After 2 washes with icecold PBS, 5 minutes per wash, cells were dehydrated in a series of methanol (25%, 50%, 75% and 100%) in PBS containing 0.1% Tween-20 (PBST). Dehydrated explants were stored at −20° C. in methanol until use. For in situ hybridization, dehydrated cells were rehydrated into PBST with series of methanol, treated with proteinase K (10 µg/ml in PBST for 3 minutes, washed twice with glycine (2 mg/ml) in PBST and post-fixed in 0.2% glutaraldehyde and 4% paraformaldehyde in PBT for 20 minutes at room temperature. Following 3 PBST washes, embryos were rinsed once with 1:1 prehybridization buffer. Following prehybridization at 70° C. with prehybridization buffer for 2 hours, cells were hybridized overnight with digoxigenin-labeled RNA probe (approximately 1 µg/ml) in hybridization buffer (same as prehybridization buffer) at 70° C. Digoxigenin-labeled RNA probe were synthesized with RNA polymerase using albumin cDNA as a template. Hybridized cells were once rinsed with pre-warmed (70° C.) prehybridization buffer, washed 3 times in prehybridization buffer, and washed in 1:1 prehybridization buffer/Tris buffered saline containing 0.1% Tween-20 (TBST) at 70° C. for 30 minutes each. Following 3 washes with TBST, cells were blocked with 2% blocking reagent (BBR) (Roche) in TBST for 1 hour and with 10% heat-inactivated normal goat serum (NGS) and 2% BBR in TBST for two hours. To prevent non-specific binding of antibody, the anti-digoxigenin Fab alkaline phosphatase conjugate (Roche) was pre-absorbed and diluted 1:2000 with 10% NGS and 2% BBR. The cells were incubated overnight with pre-absorbed antibody solution at 4° C. After 4 rinses with TBST, cells were washed 6 times in TBST for 1 hour each and overnight. Following four 10 minute washes in NTMTL (100 mM NaCl, 100 mM Tris HCl (pH9.5), 50 mM $MgCl_2$, 1% Tween-20, and 2 mM Levamisole), coloring reactions were performed in BCIP/NBT solution (3.38 µg/ml NBT (Roche Molecular Biochemicals, Mannheim, Germany) and 1.75 µg/ml BCIP (Roche Molecular Biochemicals) in NTMTL). For FASTRED staining of wild type and homozygous explants, after TBST washes the cells were washed in NTMTL (pH 8.0) and color reactions were performed in FASTRED solution. FASTRED solution was prepared using FASTRED tablets (Sigma Chemicals, St. Louis, Mo.) according to the instruction, The color development reactions were continued 1 to 6 hours. The reactions were stopped by 3 washes of PBS.

What is claimed is:

1. A method of promoting liver differentiation comprising obtaining hepatic cell precursor in which no vasculature is present;
directly contacting the hepatic cell precursor in vitro with endothelial cells;
culturing the hepatic cell precursor and endothelial cells on a Transwell membrane in culture medium comprising Dulbecco's Modified Eagle Medium, $NaHCO_3$, calf serum, and Matrigel thereby promoting liver differentiation and de novo vascular development.

2. A method of promoting de novo vascular development comprising obtaining hepatic cells in which no vasculature is present; directly contacting the hepatic cells in vitro with endothelial cells; and culturing the hepatic cells and endothelial cells; wherein the hepatic cells comprise a hepatic cell line and the endothelial cells comprise human umbilical vein endothelial cells; wherein the hepatic cells and endothelial cells are cultured in a mixture of endothelial cell medium and hepatic cell medium; wherein the endothelial cell medium comprises Endothelial Cell Basal Medium-2, hydrocortisone, hFGF-B, VEGF, R3-IGF-1, Ascorbic acid, heparin, fetal bovine serum, hEGF, and GA-1000; and the hepatic cell medium comprises Dulbecco's Modified Eagle Medium, Ham's F-12 media; fetal calf serum, and insulin.

3. The method of claim 2, wherein the endothelial cell medium and hepatic cell medium are at a ratio in the range of 1:1 to 20:1.

* * * * *